Sept. 8, 1936. C. MALLERIN Plant Pat. 191
ROSE
Filed March 4, 1936
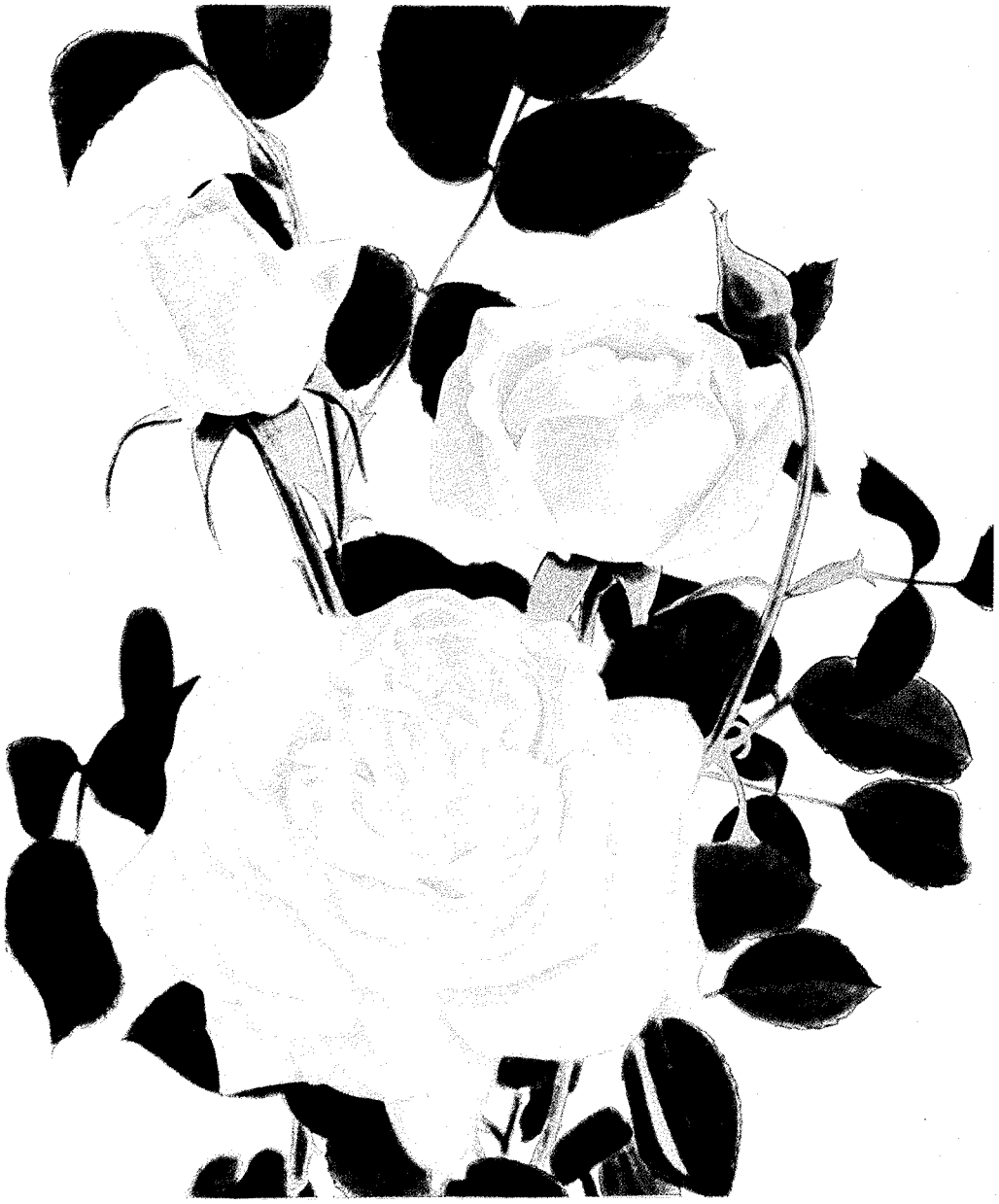
Inventor
C. Mallerin
By Robb & Robb
attorneys Patented Sept. 8, 1936

Plant Pat. 191

UNITED STATES PATENT OFFICE

191

ROSE

Charles Mallerin, Varces, France, assignor to The Conard-Pyle Company, West Grove, Pa.

Application March 4, 1936, Serial No. 67,169

1 Claim. (Cl. 47—61)

The present invention relates to a new and distinct variety of rose plant, resulting from a definite breeding having as its objective the production of a new color in garden roses.

So successful was this hybridizing that I have produced a rose of a color which is altogether different from that of any rose heretofore known and a plant that in every respect may be considered a distinct improvement over either of its parents or other roses of similar coloring characteristics.

The novelty of this new variety may be said to arise by virtue of the fact that when the bloom first opens the basic color is that of deep old rose overspread with scarlet and orange with the base of the petals orange chrome. The scarlet coloring referred to, however, as the flower ages disappears, leaving the old rose with an orange base to the petal so as to give the resulting impression of old rose flushed orange coloring in the mature stage of the bloom. Under the circumstances, the flowers of this variety present a distinctively new color in Hybrid Pernetiana roses throughout all stages of their development.

Asexual reproduction of the plant has proved the novel characteristics are fixed.

The following is a detailed description of the new variety, all reference to color being based on Ridgway's Color Chart or ordinary dictionary definitions:

Parentage:

Seed parent—Mrs. Pierre S. du Pont.

Pollen parent—Charles P. Kilham.

Classification:

Pernetiana hybrid.

*Flower*

Blooming habit:

Continuous.

Bud:

*Size.*—Medium.

*Form.*—Ovoid, pointed.

*Color.*—Orange old rose.

*Sepals.*—Wide ⅔ of length terminating in a long narrow point. Some not branched, others with one slender branch on one side only. Hug the bud.

*Calyx.*—Goblet shaped about as long as wide. Smooth, very little scent when rubbed.

*Peduncle.*—Long, strong.

*Opening.*—Opens well at all times.

Bloom:

*Size.*—4 to 4½ inches.

*Borne.*—Single.

*Stems.*—Medium length, strong.

*Form.*—Cup shaped, compact, outer petals reflex making a ball shaped bloom, stamens almost hidden by short center petals.

*Permanence.*—Long lasting.

*Petalage.*—About sixty petals.

*Color.*—When first opening the basic color deep old rose is heavily overspread with scarlet and orange, with the base of the petals orange chrome. As the flower ages the scarlet disappears leaving the old rose with an orange base to the petals, the impression is then old rose flushed orange.

Petals:

*Texture.*—Heavy, but not leathery.

*Appearance.*—Metallic.

*Form.*—Outer petals as wide as long, almost round. Inner petals pear shaped.

*Arrangement.*—Irregular giving a dishevelled appearance.

*Persistence.*—Drop off cleanly.

*Fragrance.*—Spicy fragrance.

*Lasting quality.*—Long lasting.

Genital organs:

*Stamens, anthers.*—Less than average number. Color—pale orange. Arrangement—irregular.

*Stamens, filaments (threads).*—Various lengths. Color—lemon.

*Pollen.*—Orange.

*Styles.*—Bunched, uneven length, slightly shorter than stamens.

*Stigmas.*—Upper half pink, lower half straw colored.

*Ovaries.*—Normal.

Fruit:

Variety fertile with own pollen.

*Form.*—Goblet shaped.

*Aspect.*—Smooth.

*Color at maturity.*—Apricot.

*Sepals.*—Fold back on stem.

*Plant*

Form:

Bush.

Growth:

Spreading, a little less than average height.

Foliage:

*Number of leaflets to compound leaf:* New foliage, nearest the flowers, 3; mature foliage, on lower older part of stem, 5.

*Size.*—Medium.

*Quantity.*—Average.

*Color.*—New foliage—bronzy light green, the underside very deep bronze. Mature foliage—medium green above, olive green below.

*Shape.*—Ovoid.

*Texture.*—Medium heavy.
*Edge.*—Serrated.
*Serrations.*—Even, not deep.
*Ribs and veins.*—Ordinary, lightly impressed.
*Rachis.*—Color—light green. Under side almost smooth, an occasional prickle.
*Stipules.*—Medium, bearded.
*Disease resistance.*—Subject to black spot.
Wood:
*New wood.*—Light green.
*Old wood.*—Light green.
Thorns:
*Quantity.*—Numerous.
*Form.*—Wide base almost straight.
*Color when young.*—Red.
*Position.*—Irregular.
*Prickles.*—None.
*Short needles.*—A few on new wood only.

I claim:

The new and distinct variety of rose plant characterized by the distinct color of its flowers through all stages of their development, substantially as shown and described.

C. MALLERIN.